United States Patent [19]

Freeman

[11] Patent Number: 5,283,063
[45] Date of Patent: Feb. 1, 1994

[54] PUNCTUM PLUG METHOD AND APPARATUS
[75] Inventor: Jerre M. Freeman, Memphis, Tenn.
[73] Assignee: Eagle Vision, Memphis, Tenn.
[21] Appl. No.: 830,333
[22] Filed: Jan. 31, 1992
[51] Int. Cl.$^5$ .................. A61F 2/14; A61M 35/00
[52] U.S. Cl. .................... 424/427; 514/912; 604/294; 606/107; 606/191; 623/4; D24/105
[58] Field of Search .......... 424/427; 514/912; 604/294; 606/107, 191; 623/4; D24/105

[56] References Cited
U.S. PATENT DOCUMENTS

| | | | |
|---|---|---|---|
| 3,726,284 | 4/1973 | Parker | 128/350 R |
| 3,949,750 | 4/1976 | Freeman | 424/427 |
| 4,142,526 | 3/1979 | Zaffaroni et al. | 424/428 |
| 4,660,546 | 4/1987 | Herrick et al. | 128/1 R |
| 4,801,475 | 1/1989 | Halpern et al. | 427/338 |
| 4,814,131 | 3/1989 | Atlas | 264/147 |
| 4,871,785 | 10/1989 | Froix | 523/106 |
| 4,915,684 | 4/1990 | MacKeen et al. | 604/8 |
| 4,959,048 | 9/1990 | Seder et al. | 604/8 |

OTHER PUBLICATIONS

The dry eye A working outline of etiology, symptoms, diagnosis, and treatment, W. S. Muenzler, MD, Geriatr Ophthalmol 2(1):19-23, Jan./Feb. 1986.

Temporary Intracanalicular Collagen Implant/Lactoplate, Eagle Vision, Inc, Memphis, Tenn., Oct. 1988.

Primary Examiner—Paul R. Michl
Assistant Examiner—C. Azpuru
Attorney, Agent, or Firm—Bradford E. Kile; Ruffin B. Cordell

[57] ABSTRACT

A punctum plug for blocking lacrimal fluid flow through a punctum and an associated canaliculus composed of a hydrogel material and a hydrophobic coating which covers the exterior surface of the hydrogel material. The hydrophobic coating averts adsorption of proteinaceous materials onto the hydrogel. The punctum plug has a configuration which includes a generally cylindrical body member, an arcuate head at a first end of the body member, and a placement and retaining member at a second, peripheral end of the body member. An insertion port is located at the first end of the cylindrical body member for receiving a dilator/inserter tool. A hydrating port is fashioned at the peripheral end of the plug and partially extends through the placement and retaining member. The hydrating port is not coated with the hydrophobic material so that fluid in the canaliculus, or canalicular fluid, or preocular tear film may enter the interior portion of the plug and permit the hydrogel to expand to a desired configuration.

25 Claims, 6 Drawing Sheets

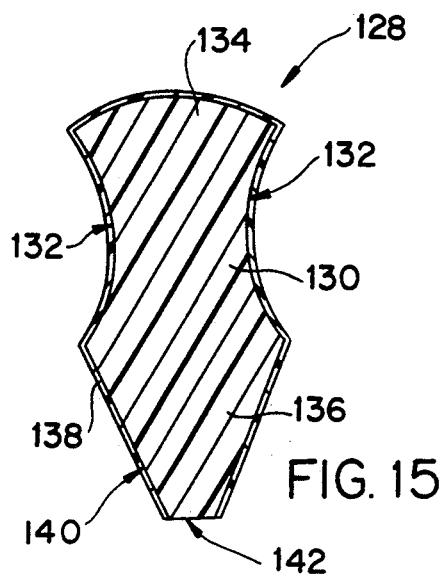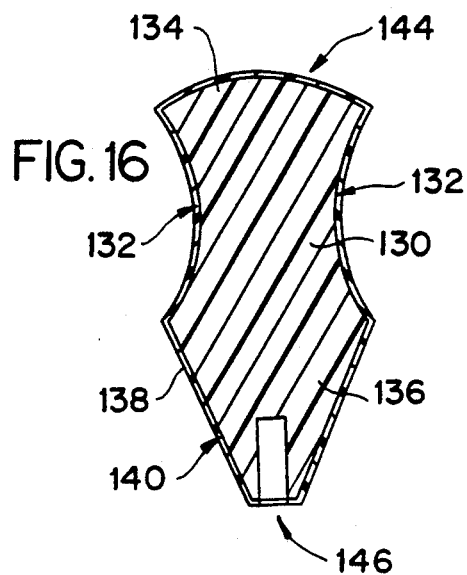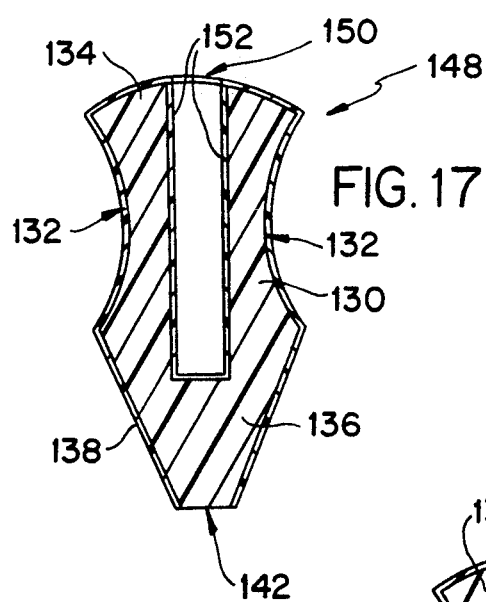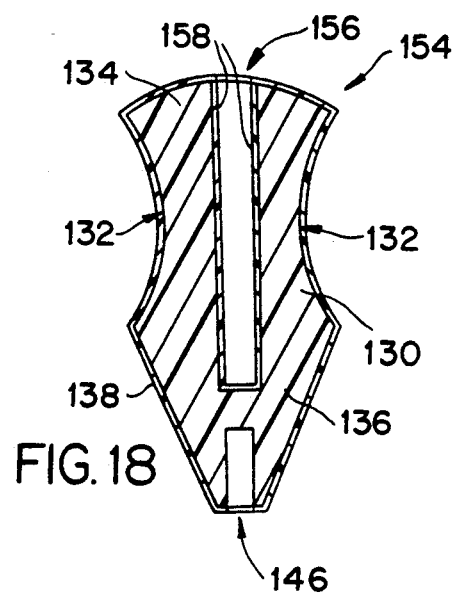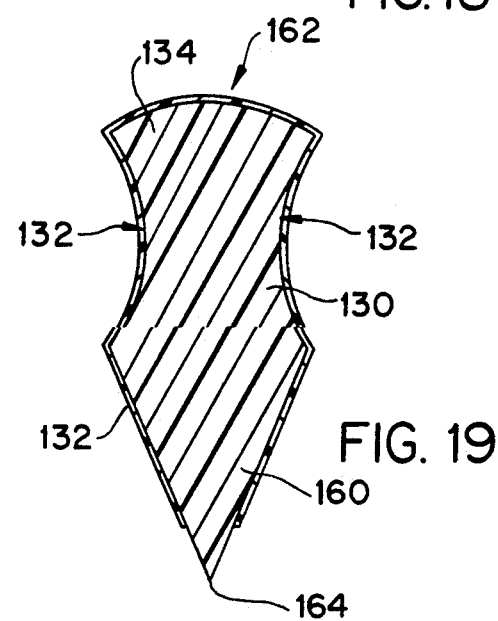

PUNCTUM PLUG METHOD AND APPARATUS

RELATED PATENT

This application is related to the subject matter of prior Freeman U.S. Pat. No. 3,949,750 entitled "Punctum Plug Method for Treating Keratoconjunctivitis Sicca (Dry Eye) and Other Ophthalmic Ailments Using Same."

BACKGROUND OF THE INVENTION

This invention relates to a novel method and apparatus for the treatment of tear-related disorders of the eye. More specifically, this invention relates to a punctum plug for treating cases of mild to moderate keratitis sicca or kertoconjunctivitis sicca (dry eye) and related disorders by occluding the flow of lacrimal fluid into the punctum and canaliculus.

In a healthy eye, movement of the upper eyelid spreads a film of tears over the corneal and conjunctival epithelia, making the eye smooth and optically clear. The tear film is composed of three layers which coat the surface of the eye. An outer, oily layer is produced by small glands called meibomian glands located at the edges of the eyelids. This outer layer provides a smooth tear surface and reduces evaporation of tears. An intermediate, watery layer is produced by a large lacrimal gland and a plurality of small glands scattered throughout the conjunctiva. This watery layer contains the largest amount of fluid and cleanses the eye by washing away foreign particles and irritants. An inner layer consists of mucus produced by goblet cells in the conjunctiva. This inner layer allows the watery layer to spread evenly over the surface of the eye. In addition, the mucus produced by the goblet cells enables the aqueous tears to wet the epithelial surface.

Normally, the preocular tear film (PTF) is formed by the cooperative interaction of products from the Meibomian glands, the lacrimal gland, and the goblet cells; however, sometimes these glands produce less than adequate amounts of tears, resulting in dry eye.

Dry eye is characterized by an inability to maintain a stable preocular tear film due to insufficient production or excessive drainage of lacrimal fluid. Dry eye describes a continuum of problems which range from discomfort, to decreased vision and pain, and, in extreme cases, to blindness. The causes of dry eye include aging, disease inflammatory processes, and prescription drug side effects.

A previous prior art practice in treating dry eye has been to utilize various types of topical drops and ointments. Some sufferers of dry eye prefer using humidifiers and vaporizers to increase the moisture level in the surrounding air, which helps by decreasing evaporation of lacrimal fluid from the eye.

More recently, permanent punctal occlusion has proven to be an effective method of treating tear-related disorders including dry eye, corneal ulcers, conjunctivitis, blepharitis, contact lens problems and other external eye diseases. In extreme cases of discomfort and pain, such as occur in Sjogren's syndrome, permanent closure of the puncta and canaliculi by surgery or cauterization has produced marked success.

Each of the aforementioned treatments, however, possess certain inherent limitations. Topical drops and ointments require frequent re-applications. Humidifiers and vaporizers are relatively bulky and must be connected to an electrical source and, thus, are not satisfactory for all occasions, such as outdoor activities. Finally, surgical or cauterization procedures are costly and create a danger of subsequent epiphora and/or infection, the destruction of normal tissue requires surgical intervention to reverse.

The foregoing noted problems of mild to moderate dry eye have been advantageously addressed by the introduction of a punctum plug which provides reversible punctal occlusion as disclosed and claimed in the previously identified Freeman U.S. Pat. No. 3,949,750. The disclosure of this patent is incorporated herein by reference as though set forth at length.

Total occlusion of a punctum with a silicone plug of the Freeman design has proved to be very beneficial to patients suffering from dry eye conditions. However, some physicians have reported that insertion of the punctum plug is occasionally difficult because of the size of the plug relative to the size of a patient's punctal opening. In this connection it is often necessary to dilate a patient's punctum for plug insertion which may cause patient anxiety and/or discomfort.

The use of polyhydroxyethylmethacrylate p(HEMA) as a plug composition has been theorized, at least in part, because in a dry state its firmness facilitates the process of insertion. Once inserted, HEMA is hydrated, becomes soft and flexible and swells to conform in shape to a patient's lacrimal duct, or canaliculus, thereby improving the closure of the punctal aperture. However, the biocompatibility of HEMA, a solid hydrogel material, has not been satisfactory. It has been determined that soluble proteinaceous substances present in the preocular tear film (PTF) and canaliculus may be absorbed into or adsorbed onto the hydrogel and denatured proteins can initiate immune responses.

The difficulties in the preceding are not intended to be exhaustive but rather are among many which may tend to reduce the effectiveness of prior known methods and devices for treatment of dry eye. Other noteworthy problems may also exist; however, those presented above should be sufficient to demonstrate that methods and devices for treating dry eye syndrome appearing in the past will admit to worthwhile improvement.

OBJECTS and BRIEF SUMMARY OF THE INVENTION

Objects

It is therefore a general object of the invention to provide a novel method and apparatus for the treatment of dry eye syndrome which will obviate or minimize difficulties of the type previously described.

It is a specific object of the invention to alleviate the symptomology of medium to moderate dry eye and related ophthalmic ailments by efficiently and effectively occluding the flow of lacrimal fluid from the surface of a patient's eye into the patient's lacrimal ducts.

It is a further object of the invention to provide a punctum plug which does not adsorb or absorb soluble proteinaceous substances present in a patient's canalicular fluids.

It is another object of the invention to provide a punctum plug which does not contain toxic substances which could effect an adverse immunological tissue response.

It is yet another object of the invention to provide a punctum plug which is easily maintained in a sterile state until the plug is inserted through the punctal aperture of a patient and into the associated canaliculus.

It is still another object of the invention to provide a punctum plug which may be facilely inserted through a patient's punctal aperture via an easily reversible procedure.

It is yet a further object of the invention to provide a punctum plug which will be securely held in position after the plug is positioned within the proximal portion of canaliculus of a patient.

It is yet still another object of the invention to provide a punctum plug which, when in an operative position, is unobtrusive and minimizes patient discomfort.

BRIEF SUMMARY OF THE INVENTION

A preferred embodiment of the invention which is intended to accomplish at least some of the foregoing objects comprises a punctum plug including a generally cylindrical body member composed of a hydrogel material and having a first end operable to be positioned adjacent a patient's punctal aperture and a second end operable to be positioned through the punctal aperture and into an associated canaliculus. A head member, also composed of the hydrogel material, is integrally joined to the first end of the body member. The diameter of the head member at the junction with the body member has a greater diameter than the body member to form an annular ridge between the head member and the body member. The annular ridge rests on the surface surrounding the punctal aperture to prevent the punctum plug from migrating into the associated canaliculus. A placement and retaining member composed of the hydrogel material is integrally joined to the second end of the body member for facilitating placement of the body member through the punctal aperture and for retaining the body member within the associated canaliculus.

A hydrophobic coating covers the exterior surface of the head member, the body member, and the placement and retaining member to isolate the hydrogel material from physical contact with the canalicular and ocular tissue of the patient.

A hydrating means, in the form of a hydrating port or a hydrating bore, is fashioned through the hydrophobic coating for permitting placement of the punctum plug into position in a dehydrated, relatively rigid condition and then permitting, in situ, hydration of the hydrogel material of the punctum plug. The hydrating means serves to admit lacrimal fluid into the hydrogel material to hydrate the punctum plug into an expanded, relatively flexible condition. In addition, the hydrophobic coating may be advantageously selected to be permeable to lacrimal fluid.

The punctum plug may also include an insertion bore for receiving an insertion tool. The insertion bore preferably extends into the head member coaxially with respect to the body member, and, depending upon the particular punctum plug, may or may not be coated with the hydrophobic coating.

A method of manufacturing a punctum plug in accordance with the invention includes the steps of molding a hydrogel material into a desired punctum plug configuration; hydrating the hydrogel material to remove toxic substances from the interstices of the hydrogel material; drying the exterior surface of the hydrogel material; applying a flexible hydrophobic coating to the exterior surface of the hydrogel material; and dehydrating the hydrogel material to create a final condensed hydrogel material which is surrounded by a hydrophobic coating.

A method of blocking the flow of lacrimal fluid though a punctum and into an associated canaliculus of a human eye in accordance with the invention includes the steps of inserting a hydrogel punctum plug having a hydrophobic coating into a patient's punctal aperture; hydrating the punctum plug with the aid of a port through the hydrophobic coating and body fluid seeping through the port to swell the hydrogel punctum plug, in situ, to an occluding state with the associated canaliculus; and isolating the hydrogel punctum plug from physical contact with a patient's punctal aperture and associated canaliculus with the hydrophobic coating to prevent irritation, infection, and exciting an allergic ocular response then while concomitantly occluding a patient's canaliculus.

THE DRAWINGS

Other objects and advantages of the present invention will become apparent from the following detailed description of a preferred embodiment thereof taken in conjunction with the accompanying drawings, wherein:

FIG. 15 is a detailed cross-sectional view of a fifth embodiment of a hydratable punctum plug of the present invention;

FIG. 16 is a detailed cross-sectional view of a modification of the embodiment of the hydratable punctum plug shown in FIG. 15;

FIG. 17 is a detailed cross-sectional view of a further modification of the embodiment of the hydratable punctum plug shown in FIG. 15;

FIG. 18 is a detailed cross-sectional view of another modification of the embodiment of the hydratable punctum plug shown in FIG. 15;

FIG. 19 is a detailed cross-sectional view of a sixth embodiment of a hydratable punctum plug of the present invention.

DETAILED DESCRIPTION

Context of the Invention

Figure 1:
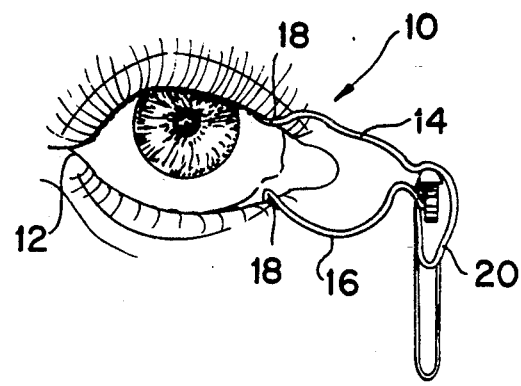
FIG. 1 is an axonometric view, partially broken away, disclosing the anatomy of a human eye including the upper and lower lacrimal ducts or canaliculi which operably connect to a lacrimal sac and ultimately a nasal passage.

Before discussing in detail a method and apparatus for occluding the passage of lacrimal fluid into a patient's lacrimal ducts, or canaliculi, with a hydratable punctum plug, it may be useful to briefly discuss the context of the invention in association with FIG. 1. More specifically, the anatomy of a human eye 10 is illustrated including an outer corneal surface 12 which is lubricated by a thin preocular tear film, or PTF, which coats the surface of the eye. This thin film is composed of three layers: an outer, oily layer; an intermediate, watery layer; and an inner layer of mucus.

Maintaining a PTF over the eye by blinking makes the surface of the eye smooth and optically clear. In instances where the tear film is not adequate, a patient may encounter symptoms of stinging, burning, scratchiness, stringy mucus and excess irritation. Moreover, tear deficiencies cause chronic irritation of the anterior segment of the eye and result in symptomology of sandy itching eye, conjunctivitis, metabolic disturbances of the cornea, and, in extreme cases, a loss of visual function.

Tears which lubricate the eye are continually produced by small glands scattered throughout the conjunctiva, which is the delicate membrane lining the inside of the eyelid and covering a significant portion of the eyeball. Excessive tearing is drained away from the eye surface through an upper 14 and lower 16 lacrimal duct via punctal apertures 18. The lacrimal ducts 14 and 16, better known as the canaliculi, converge into a lacrimal sac 20 which leads to the nasal cavity.

In order to alleviate the symptomology of medium to moderate dry eye and related ophthalmic ailments, a punctum plug of the present invention may be inserted through a patient's punctal aperture and into an associated canaliculus to efficiently and effectively occlude the flow of lacrimal fluid from the surface of the patient's eye into the patient's lacrimal ducts.

Hydratable Punctum Plug

Figure 2:
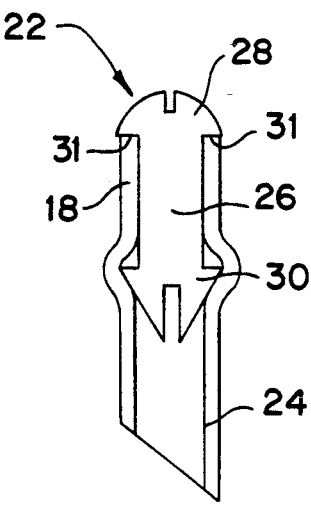
FIG. 2 is a detailed cross sectional view of a punctum and associated canaliculus of a human eye, such as illustrated in FIG. 1, with a hydratable punctum plug positioned within the canaliculus according to the present invention.

Referring now to the drawings, wherein like numerals indicate like parts, and initially to FIG. 2, there will be seen a punctum plug 22 of the instant invention in an operative context. The punctum plug 22 is inserted through a punctal aperture 18 (note also FIG. 1) and into an associated canaliculus 24 to block lacrimal fluid flow through the punctal aperture and into an associated canaliculus. The punctum plug 22 may be operably inserted into either the upper or the lower canaliculus 14 and 16, respectively, or both.

The punctum plug 22 includes a generally cylindrical body member 26, a head member 28 integrally joined to a first end 25 of the body member 26, and a placement and retaining member 30 integrally joined to a second end 27 of the body member 26. In an operative position, the first end 25 of the body member 26 is positioned adjacent the punctal aperture 18, and the second end 27 is positioned through the punctal aperture 18 and into the canaliculus 24. The head member 28 rests on a surface 31 surrounding the punctal aperture 18 to prevent the punctum plug 22 from migrating into the canaliculus 24. The placement and retaining member 30 extends away from the punctal aperture 18, in situ, and blockingly protrudes into a generally vertical portion of a patient's canaliculus 24.

Figure 3:
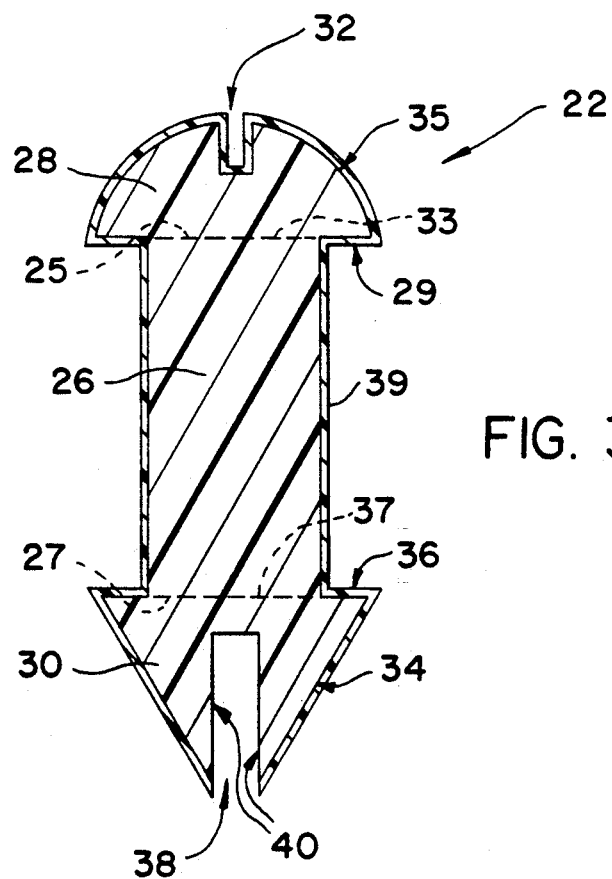
FIG. 3 is a detailed cross-sectional view of one embodiment of a hydratable punctum plug of the present invention.

Turning to FIG. 3, the structural configuration of an embodiment of the hydratable punctum plug 22 will now be described. The head member 28 of the punctum plug 22 is hemispherical in shape and has a base 33 integrally joined to the first end 25 of the body member 26. The exterior diameter of the base 33 of the head member 28 is greater than the diameter of the cylindrical body member 26 to form an annular ridge 29. When the plug 22 is inserted through a patient's punctal aperture, the annular ridge 29 operably rests upon a patient's punctal opening 18. The head member also has an arcuate surface 35 extending away from the first end 25 of the body member 26.

An insertion bore 32 partially extends into the hemispherical head member 28 in a direction coaxial with the generally cylindrical body member 26. The insertion bore 32 permits an insertion tool (not shown) to engage the punctum plug 22 and thereby facilitate insertion of the plug 22 through the punctal aperture of a patient and into the associated canaliculus.

The placement and retaining member 30 is integrally joined to the second end 27 of the generally cylindrical body member 26 by a base 37. This placement and retaining member 30 is advantageously formed in the configuration of a truncated cone and is fashioned with a conical exterior surface 34 which projectingly directs placement of the punctum plug 22 into a patient's canaliculus. The diameter of the base 37 of the placement and retaining member 30 is greater than that of the cylindrical body member 26 to form a second annular ridge 36. The second annular ridge 36 serves to retain and immobilize the plug 22 in the canaliculus so that the plug is not easily dislodged by the wearer.

The head member 28, the generally cylindrical body member 26, and the placement and retaining member 30 are composed of a solid hydrogel, or any other suitable hydratable material, which is relatively rigid in a dehydrated state and which will hydrate and expand when placed in contact with lacrimal fluid from a patient's eye. Hydratable materials which would be suitable in the practice of the present invention would be well-known by those of ordinary skill in the art. A hydrogel composed of hydroxyethylmethacrylate, which is a hydrophilic polymer, is preferred in the practice of the present invention.

A hydrophobic coating 39 covers the exterior surfaces of the head member 28, the body member 26, and the placement and retaining member 30 to isolate the canalicular and ocular tissue of a patient from the hydrogel material. The hydrophobic coating 39 prevents the adsorption of soluble proteinaceous materials from the canalicular tissue, and lacrimal fluid or preocular tear film onto the exterior surface of or within the hydrogel. The coating is preferably composed of a flexible polymer, such as a medical-grade silicone, to prevent cracking during manipulation of the plug 22. In addition, in certain instances, the coating may be permeable to lacrimal fluid to hydrate the punctum plug by osmosis through the coating provided a material is selected to maintain physical isolation of the hydrogel material from the surrounding canalicular or ocular tissue.

A hydrating feature fashioned through the hydrophobic coating 39 serves to admit lacrimal fluid into the hydrogel material of the punctum plug 22 to hydrate the plug into an expanded, relatively flexible condition. In the embodiment shown in FIG. 3, a hydrating bore 38 extends through the hydrophobic coating 39 and into the placement and retaining member 30 in a direction coaxial with respect to the cylindrical body member 26. When the punctum plug 22 is operably inserted into the canaliculus of a patient, lacrimal fluid permeates a cavity wall 40 of the hydrating bore 38 due to osmotic pressure and operably hydrates the hydrogel interior of the plug 22. Thus, the combination of a hydrogel material surrounded by hydophobic coating and a hydrating feature fashioned through the hydrophobic coating permits placement of the punctum plug into position in a dehydrated, relatively rigid condition and then permits, in situ, hydration of the hydrogel material to swell the plug to a relatively flexible condition.

As noted earlier, the hydrophobic coating material of the present invention must be flexible and conform in shape to the underlying dehydrated hydrogel to facilitate the insertion process. Any hydrophobic coating material may be used in the practice of the present invention as long as it is compatible with the tissues of the eye and it is able to prevent the adsorption and absorption of soluble proteinaceous materials from the canalicular tissue or Preocular Tear Film (PTF) onto the exterior surface of or into the hydrogel. A wide variety of hydrophobic coating materials are suitable in the practice of the present invention. Suitable hydrophobic coating materials include fluorocarbon polymers, polyamides, polyesters, fluorocarbon silanes, fluorocarbon epoxides, fluorocarbon polyethers and the like. While a complete list of every type of hydrophobic coating material can be found in any standard reference text on polymers, such as Billmeyer, Fred W. Jr., "Textbook of Polymer Source", John Wiley & Sons, Inc. (1962), a brief description of several suitable classes of hydrophobic polymers is set forth below.

Silicone rubber is known by a number of names including silicone resin, organopolysiloxane and silicone elastomers. Silicone rubbers are polycondensation rubbers which consist of a backbone of alternating silicone and oxygen atoms to which organic radicals are attached.

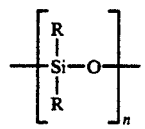

The members differ from each other mainly in the nature of the organic substituents on the silicon atoms and the degree of polymerization. In the absence of double bonds in the backbone, the many forms of stereoisomers found in the unsaturated hydrocarbon rubbers lack counterparts in silicone rubbers. Silicone fluids such as dimethylpolysiloxane fluids have a specific gravity of about 0.761–0.975 (at 25 degrees C. referred to water at 25 degrees C.).

A wide variety of silicone materials are now known in the art. Any polymerized silicone polymer would be a suitable coating material. In particular, Q7-4840, Q7-4850, Q7-4865, Q7-4750 Q7-4760 Q7-4730 Sylguard-104, Sylguard-106 and the like by Dow Corning may be mentioned.

Fluorocarbon polymers as a class possess in varying degrees chemical inertness and thermal stability due to the shielding effect of the bulky fluorine atome. The fluorocarbons are much more dense than hydrocarbons and have densities in the region of 2. They exhibit very low viscosities and high vapor pressures in relation to their molecular weights. The fluorocarbons have the lowest refractive indices of any chemical class and are highly transmissive to visible and near infrared light. The fluorocarbon polymers have high chemical and thermal inertness, as well as excellent electrical, low friction and anti-stick properties.

The term "fluorocarbons," strictly defined, refers to compounds containing only carbon and fluorine. In common practice, however, "fluorocarbon" and "fluorocarbon polymer" are used in reference to materials whose properties reflect the presence of a significant fluorine content. Of course, these "fluorocarbon-like" properties are progressively diluted and lost as one replaces fluorine atoms with hydrogen or chlorine atoms in any fluorocarbon structure. The weaker carbon-hydrogen and carbon-chlorine bonds provide points more vulnerable to chemical attack or initiation of thermal decomposition.

Many different fluorocarbon polymers have been synthesized. For example, many monomeric fluorocarbon compounds and derivatives have been converted into polymers by polymerization reactions analogous to those familiar to the polymer chemist. Typical of these are the fluorocarbon acrylates such as heptafluorobutyl acrylate:

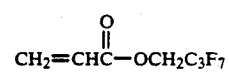

Here the perfluoroalkyl group does not appreciably affect the polymerization behavior characteristic of the acrylate esters but is strategically placed so as to confer solvent-resistant properties upon the elastomer that results:

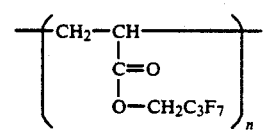

Polyamides and polyesters can be synthesized by polycondensation of fluorocarbon dicarboxylic acid chlorides with diamines or diols, as seen below:

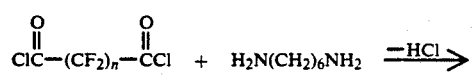

-continued

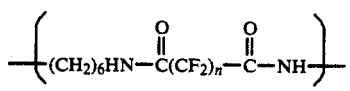

Depending upon the choice of monomers, such polycondensations can give rise to physically strong thermoplastics or elastomers.

Fluorocarbon silanes have been successfully polymerized to fluorine-containing silicones:

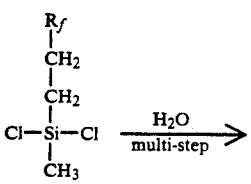

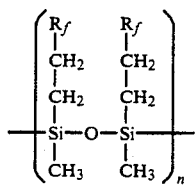

It is necessary to introduce methylene groups between the Rf (perfluoroalkyl) and the silicon to provide stability. Fluorocarbon silicones are commercially available as "LS-Silastics" by Dow Corning Corporation.

The fluorocarbon epoxides can be ring-opened to give rise to liquid polymeric ethers which are particularly useful as lubricants at high temperature:

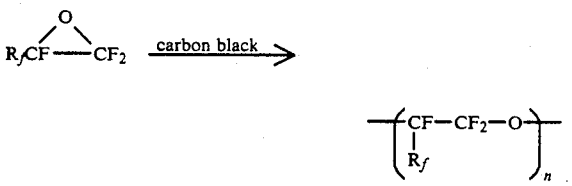

Fluorocarbon polyethers have also been prepared by workers at the Montecantini Company by a reaction between perfluoroolefins and oxygen in the presence of ultraviolet light.

In addition to the reactions which bear a similarity to those of conventional organic polymer chemistry, certain fluorocarbon derivatives form polymers by reactions which have no parallel. For example, trifluoronitrosomethane will copolymerize spontaneously with fluorocarbon olefins at very low temperatures to yield elastomeric, high molecular weight polymers. This reaction proceeds by a free radical mechanism in which $CF_3NO$ is its own initiator. These polymers are useful because they remain rubbery at low temperatures ($T_g = -60°$ F.) and resist chemical and solvent attack.

The fluorocarbon polymers may be those which are derived from the addition homopolymerization of partially and wholly fluorinated olefins, that is, ethylene monomers. Preferred fluorocarbon polymers include fluorocarbons, notably polytetrafluoroethylene (PTFE) and fluorinated ethylene propylene (PFEP); chlorofluorohydrocarbons, notably polychlorotrifluoroethylene (PCTFE); and fluorohydrocarbons, including polyvinylindene fluoride ($PVF_2$), polyvinyl fluoride (PVF), polyhexafluoropropene and copolymers of fluorinated and halogenated ethylenes. The more preferred fluorocarbon polymers intended in the practice of the present invention are the fluorocarbons, specifically, polytetrafluoroethylene (PTFE) and fluorinated ethylene propylene (PFEP).

Each of the fluorocarbon polymers have different properties. For instance, polyvinylidene fluoride has a specific gravity of 1.76, polychlorotrifluoroethylene has a specific gravity of 2.12 (770° F.), and polytetrafluoroethylene and polyperfluoroethylenepropylene each have a specific gravity of 2.15.

Both PTFE and PFEP resins are available in several forms, including film, filament, and dispersions. These resins are highly resistant to attack by chemicals and are quite stable at high temperatures. The resins have a low dielectric constant, low dielectric loss, low coefficient of friction, and very desirable antisticking characteristics.

Because PTFE resins have a high melt viscosity, they cannot be processed in conventional molding and melt-extrusion equipment. The processes used are similar to the techniques for making powder-metal parts. Unlike PTFE, PFEP is a true thermoplastic, and conventional molding and fabrication methods can be used. Both types of resins can be modified through the addition of filler and reinforcing materials.

Polytetrafluoroethylene is a preferred fluorocarbon polymer used in coating the surfaces of the present invention.

Polytetrafluoroethylene ——$CF_2$—$CF_{2n}$ is an opaque, waxy crystalline polymer which is available under the following trademarks: Teflon by DuPont, Halon by Allied Chemical and Tetran by Pennsalt.

Figure 4:
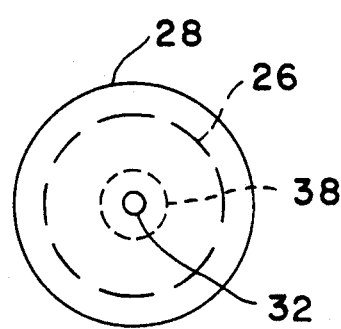
FIG. 4 is a top plan view of the hydratable punctum plug shown in FIG. 3.

Turning now to FIG. 4, a top plan view of the punctum plug 22 is shown and illustrates the relative diameters of the components of the punctum plug. The cylindrical body member 26, shown by a hatched circle, has a diameter less than the arcuate head member 28 and the placement and retaining member 30. The hydrating bore 38 has a greater diameter than the insertion bore 32.

Figure 5:
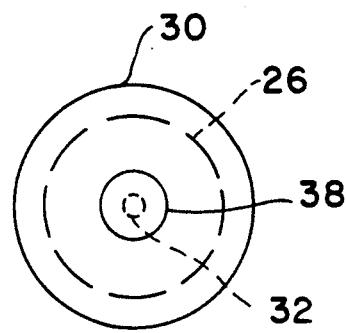
FIG. 5 is a bottom plan view of the hydratable punctum plug shown in FIG. 3.

FIG. 5 shows a bottom plan view of the punctum plug 22 in accordance with a preferred embodiment of the invention. The perimeters of the components of the invention are shown as enumerated in association with FIG. 3.

Figure 6:
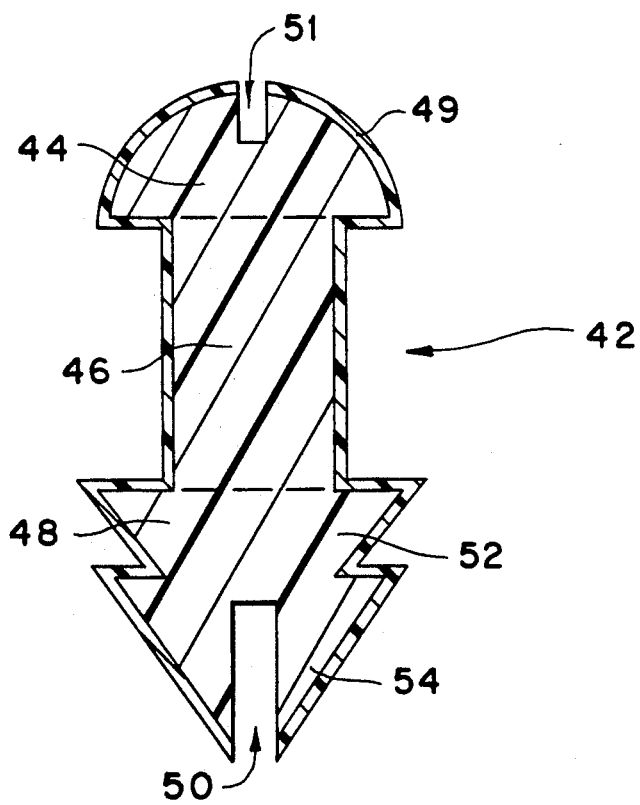
FIG. 6 is a detailed cross-sectional view of a second embodiment of a hydratable punctum plug of the present invention.

FIG. 6 illustrates a detailed cross-sectional view of a second embodiment of the present invention. A hydratable punctum plug 42 is shown having an arcuate head member 44, a generally cylindrical body member 46, and a multi-stepped placement and retaining member 48. The placement and retaining member 48 includes a cone-shaped portion 54 extending away from the generally cylindrical body member 46 and a stepped portion 52 formed in the shape of a truncated cone. The stepped portion 52 is positioned between the body member 46 and the cone-shaped portion 54. Utilization of the two stepped portions 52 and 54 provides an alternative means of placing and retaining the hydratable punctum plug 42 in the canaliculus of a patient.

A hydrating bore 50 extends through the hydrophobic coating 49 and into the placement and retaining member 48. An insertion bore 51, which extends axially into the head member 44, also penetrates through the hydrophobic coating 49 to operably admit lacrimal fluid into the head member 44 to swell the dimensions of the plug 42. The hydrating bore 50, in combination with the insertion bore 51, facilitates a rapid hydration process from both ends of the punctum plug. The material composition of the hydratable punctum plug 42 is the same as that of the punctum plug 22 described in relation to FIG. 3.

Figure 7:
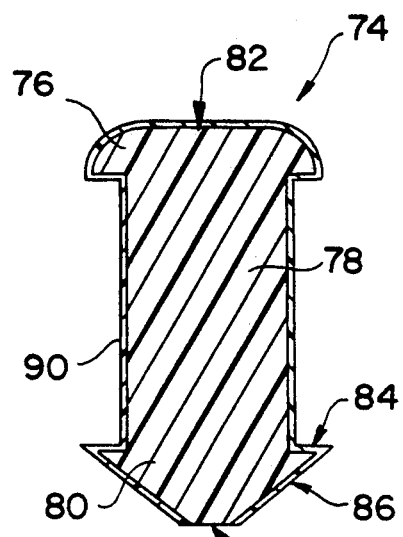
FIG. 7 is a detailed cross-sectional view of a third embodiment of a hydratable punctum plug of the present invention.

In a third alternative embodiment as shown in FIG. 7, a punctum plug 74 includes a head member 76, a generally cylindrical body member 78, and a placement and retaining member 80. The head member 76 has a generally planar central exterior surface 82 and a reduced height dimension as compared to the previously described plug embodiments. More specifically, the height dimension of the head member 76 is less than one-third the diameter of the cylindrical body member 78. This reduced height dimension may be more comfortable for patients having extremely sensitive eyes. In addition, the planar exterior surface 82 and the reduced height of the head member 76 decreases the likelihood of a patient accidentally dislodging the punctum plug 74 by rubbing his eyes. Moreover, the head member 76 is unobtrusive to a casual observer.

The placement and retaining member 80 of the punctum plug 74 shown in FIG. 7 is shaped as a truncated cone and has a base defined by annular ridge 84, a conical surface 86 extending away from the cylindrical body member 78, and a distal end 88 opposite the base. A port extends through the hydrophobic coating 90 at the distal end 88 of the placement and retaining member 80. The port serves to admit lacrimal fluid from the canaliculus of a patient into the hydrogel material of the punctum plug 74.

Figure 8:
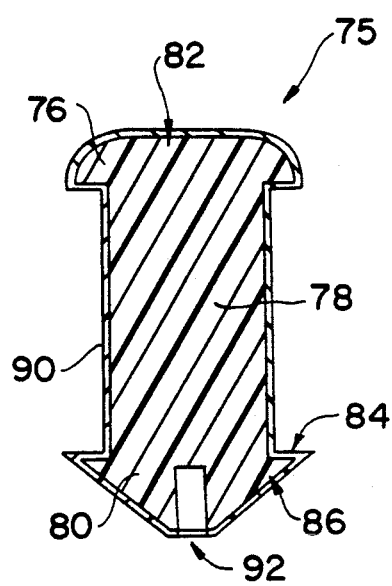
FIG. 8 is a detailed cross-sectional view of a modification of the embodiment of the hydratable punctum plug shown in FIG. 7.

The punctum plug 75 of FIG. 8 is identical in configuration to the plug 74 FIG. 7 with the exception of the port located at the distal end 88 of the plug 74 which has been replaced by a hydrating bore 92. The hydrating bore 92 extends through the hydrophobic coating 88 and into the placement and retaining member 80 in a direction coaxial with respect to the generally cylindrical body member 78. Lacrimal fluid from the canaliculus of a patient may enter the hydrogel material of punctum plug 75 through the interior sidewalls of the hydrating bore 92 to swell the punctum plug 75 to an expanded, relatively flexible condition.

Figure 9:
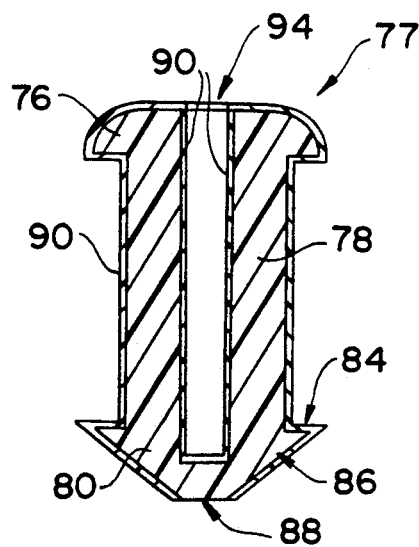
FIG. 9 is a detailed cross-sectional view of a further modification of the embodiment of the hydratable plug shown in FIG. 7.

Turning to FIG. 9, the punctum plug 77 is essentially identical in structure to the plug 74 shown in FIG. 7 and further includes an insertion bore 94 for receiving an insertion tool. The insertion bore 94 extends axially into the head member 76 and the generally cylindrical body member 78 and further extends partially into the placement and retaining member 80. In this embodiment, the insertion bore 94 is provided with the hydrophobic coating 88, although an insertion bore without a coating, yet similar in structure to insertion bore 94, is encompassed within the scope of this invention.

Figure 10:
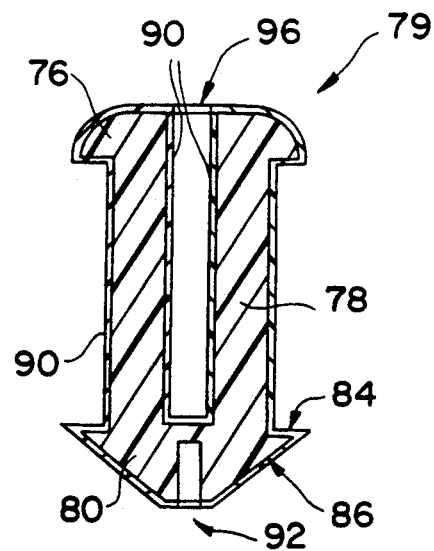
FIG. 10 is a detailed cross-sectional view of another modification of the embodiment of the hydratable punctum plug shown in FIG. 7.

In another alternative embodiment, the punctum plug 79 of FIG. 10 is structurally similar to that of FIG. 8 and includes an insertion bore 96. The insertion bore 96 extends axially through the head member 76 and partially through the generally cylindrical body member 78. The insertion bore 96 is coaxial with the hydrating bore 92 and, like the insertion bore 94 of FIG. 9, is coated with the hydrophobic coating 90.

Figure 11:
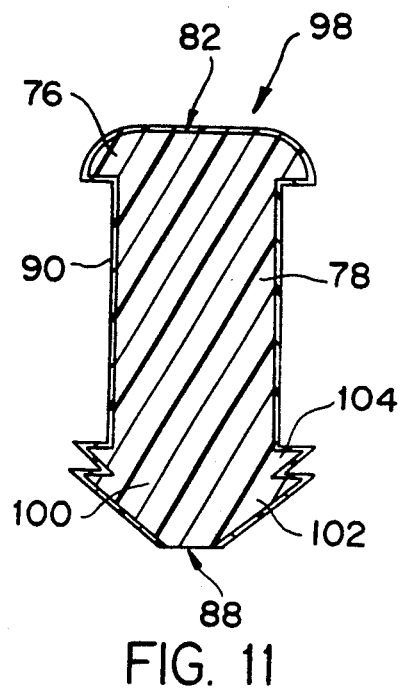
FIG. 11 is a detailed cross-sectional view of a fourth embodiment of a hydratable punctum plug of the present invention.

Turning now to FIG. 11, the punctum plug 98 is similar in structure to the plug 74 of FIG. 7 with the exception of the configuration of the placement and retaining member 100. In FIG. 11, the placement and retaining member 100 is multi-stepped and includes a cone-shaped portion 102 extending away from the generally cylindrical body member 78. A stepped portion 104 is formed in the shape of a truncated cone is positioned between the body member 78 and the cone-shaped portion 102. The placement and retaining member 100 shown in FIG. 11 is indentical to the placement and retaining member 48 described above in relation to FIG. 6.

Figure 12:
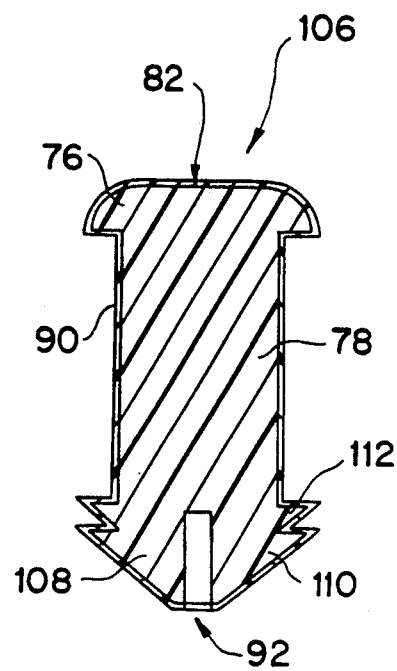
FIG. 12 is a detailed cross-sectional view of a modification of the embodiment of the hydratable punctum plug shown in FIG. 11.

Likewise, the punctum plug 106 in FIG. 12 is similar in structure to the punctum plug 75 of FIG. 8 with the exception of the placement and retaining member 108 which includes multi-stepped portions 110 and 112.

Figure 13:
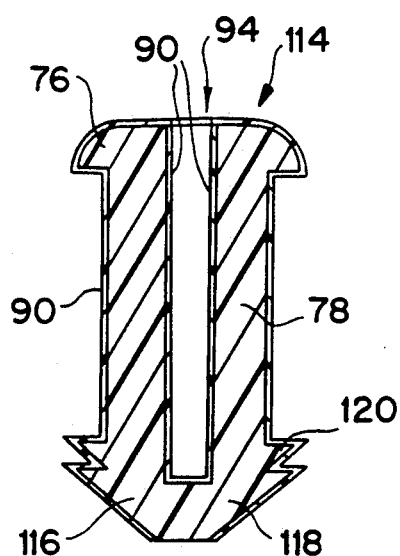
FIG. 13 is a detailed cross-sectional view of a further modification of the embodiment of the hydratable punctum plug shown in FIG. 11.

FIG. 13 illustrates a punctum plug 114 essentially the same in structure as the punctum plug 77 of FIG. 9 with the exception of the multi-stepped placement and retaining member 116. The placement and retaining member 116 includes a cone-shaped portion 118 and a stepped portion 120 formed in the shape of a truncated cone.

Figure 14:
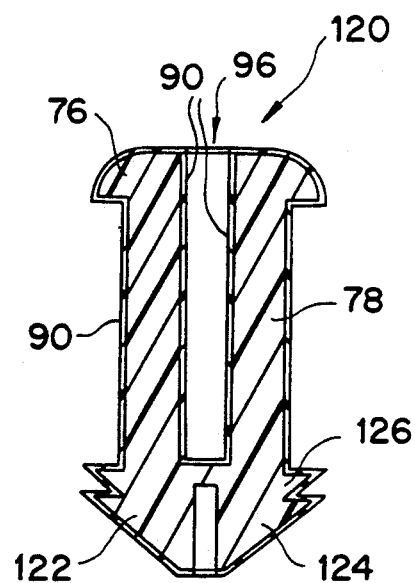
FIG. 14 is a detailed cross-sectional view of another modification of the embodiment of the hydratable punctum plug shown in FIG. 11.

In a similar vein, FIG. 14 illustrates a punctum plug 120 similar in configuration to the plug 79 shown in FIG. 10 excepting the shape of the placement and retaining member 122 which includes a cone-shaped portion 124 and a stepped portion 126. Otherwise, the structure of the punctum plug 120 mimics that of the plug 79.

A fifth set of embodiments of the subject punctum plug are illustrated in FIGS. 15-18. With specific reference to FIG. 15, a punctum plug 128 is shown which includes a generally cylindrical body member 130 having an arcuate and concave lateral side surface 132. The lateral side surface is dimensioned to generally conform to and mate to subjacent punctal tissue of a patient's eye. An arcuate head member 134 is integrally joined to a first end of the body member 130 for positioning adjacent an exterior surface of the patient's punctal aperture. A placement member 136, formed in a truncated cone shape, is integrally joined to a second end of the body member 130. The placement member 136 has a conical exterior surface 140 extending away from the body member 130 and terminates in a distal end 142. The placement member 136 facilitates placement of the body member 130 through the punctal aperture and into the associated canaliculus of a patient by channeling the distal end 142 of the plug 128 into and through the punctal aperture.

A hydrophobic coating 138 covers the exterior surface of the head member 134, the body member 130, and the placement member 136. A port is fashioned through the hydrophobic coating 138 at the distal end 142 of the placement member 136 to admit lacrimal fluid into the hydrogel material of the plug 128.

FIG. 16 shows a punctum plug 144 similar in configuration to the plug 128 shown in FIG. 15 with a hydrating bore 146 extending through the hydrophobic coating 138 and into the placement member 136. The hydrating bore 146 is coaxial with respect to the body member 130. Lacrimal fluid may penetrate the sidewalls of the hydrating port to swell the hydrogel material of the plug 144.

Focusing on FIG. 17, a punctum plug 148 is shown similar in configuration to the punctum plug 128 shown in FIG. 15 and including an insertion bore 150 for receiving an insertion tool to insert the plug 148 into a patient's punctal aperture. The insertion bore 150 extends axially through the arcuate head member 134 and the body member 130 and further extends partially into the placement member 136. The insertion port is coaxial with respect to the body member 130. In addition, the hydrophobic coating 138 extends into and covers the interior surfaces 152 of the insertion bore 150.

FIG. 18 shows a punctum plug 154 similar in configuration to the same shown in FIG. 16 and including an insertion bore 156 which extends axially through the head member 134 and partially through the body member 130. The insertion bore 156 is coaxial with the hydrating bore 146 and, depending upon the particular ailment and patient, may or may not be coated with the hydrophobic coating 138. Here, the interior surfaces 158 of the insertion bore 156 are covered with the hydrophobic coating.

In a modification of the punctum plug 128 shown in FIG. 15, the conical-shaped placement member 160 of the punctum plug 162 shown in FIG. 19 terminates in a tip 164. The tip 164 extends through a port formed through the hydrophobic coating applied to the exterior surfaces of the head member 134, the body member 130, and the placement member 160.

It is to be understood that the embodiments described in conjunction with FIGS. 7-19 are constructed using a hydrogel material and a hydrophobic coating similar in composition to the same described in association with FIG. 3.

The hydratable punctum plug of the present invention is packaged and delivered to a physician in an unhydrated state so that insertion of the plug may be performed with minimal punctal dilation. In an unhydrated state, the hydrogel material of the plug, which is fabricated from a hydrophilic polymer such as HEMA, is condensed from its operable hydrated configuration. Since the hydrophobic coating is flexible, it may adhere to portions of the dehydrated hydrogel and conform in shape to the dehydrated hydrogel.

In an operative environment, fluid present in the canaliculus flows through the hydrating port or bore, and, in some embodiments, the insertion bore. The absorbed lacrimal fluid spreads through the hydrogel material by osmosis so that the hydrogel material expands. After the hydratable punctum plug has expanded against the walls of the canaliculus, the passage of lacrimal fluid from the surface of the patient's eye into the canaliculus is occluded. The lacrimal fluid is thus maintained on the surface of the eye to relieve the symptoms of dry eye.

The hydrophobic coating, which is preferably fabricated from medical grade silicone, prevents the HEMA plug from developing a surface coating of adsorbed denatured protein so that no related adverse reactions can occur between the tissue and the hydrogel.

Method of Manufacture

In connection with the above described punctum plug, it may be useful to describe the associated method of manufacture. It should be understood that the following steps described are illustrative, rather than limiting.

The first step in fabricating the subject punctum plug is to mold or form a hydratable polymer, such as HEMA or any other suitable hydrogel, into the desired configuration as disclosed in FIGS. 3 and 6 described above. Manufacture of the structural component of the invention is made to normal specifications by conventional fabrication methods, such as injection molding, casting, compression molding, thermoforming, lathing etc.

The second step of the method of manufacture is to fully hydrate the hydrogel material so that all toxic substances, such as monomers, are removed from the interstices of the expanded hydrogel structure.

In the third step, the exterior surface of the hydrated material is dried sufficiently to permit application of a coating. The coating is applied by any suitable conventional method, such as spraying, brushing, dipping, etc. As described above, the coating is applied to all exterior surfaces of the hydrogel except the hydrating ports. The insertion port is preferably coated to prevent dirt, debris and the like from entering the interior of the plug and causing blockages which may affect the hydrated configuration of the plug. The coating should be hydrophobic or otherwise refractory to the adsorption of soluble proteinaceous material.

The hydrophobic coating may be applied to the hydrogel material in a number of conventional methods available to those skilled in the laminating and coating arts involving polymer plastics. One such method employs a thermally shrinkable tube of polymer, such as polytetrafluoroethylene, which is applied to the hydrogel material and then shrunk into contact with the hydrogel material.

Another avenue open is to apply the hydrophobic polymer as a dispersion of extremely fine particles in a carrier and apply the dispersion by brushing, dipping, or spraying the substrate surface and forming an adherent film thereon.

As indicated, a number of techniques are available and known to those skilled in the laminating and coating arts for applying the hydrophobic polymer to the hydrogel material of the present invention.

In the fourth and final step, the hydrogel material is dehydrated. The final product comprises a condensed hydrogel material which is surrounded by a hydrophobic coating.

Method of Insertion

Referring now to FIGS. 20A-20E, there will be seen a sequence of views suitable for use in inserting a punctum plug into the punctum and associated canaliculus of a patient. The insertion method is essentially the same for the punctum plugs 22 and 42 of FIGS. 3 and 5, respectively, but will here be in reference to FIG. 3 specifically.

Figure 20A:
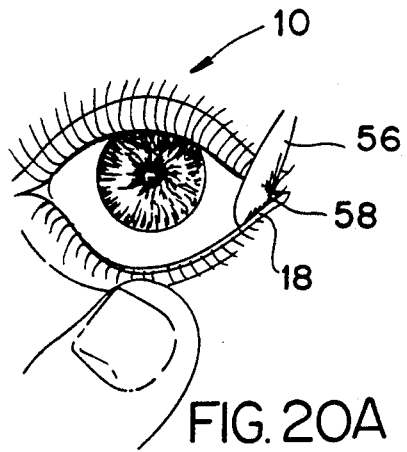
FIGS. 20A-20E disclose a sequence of installation steps of a hydratable punctum plug in accordance with the present invention.

FIG. 20A illustrates the application of a topical anesthetic, such as lidocaine, by use of a cotton tip applicator 56. The anesthetic is applied on the area of the punctal opening 18 of a patient's eye 10. As an alternative, proparacaine HCl (e.g. Ophthaine, Ophthetic) may be inserted into the area 58 of a patient's eye adjacent to the punctal opening 18.

Figure 20B:
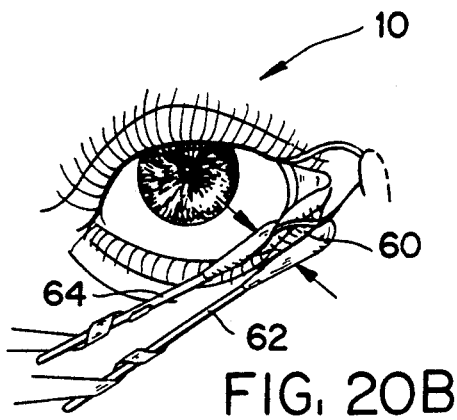

After anesthesia is adequate, the punctal zone 60 is grasped between two cotton tip applicator forceps 62 and 64 and slightly rotated to an open posture, as shown in FIG. 20B.

A punctum plug is inserted into the punctal aperture by the use of a combination dilator/inserter tool. Examples of appropriate dilator/inserter tools may be found by referring to Freeman U.S. Pat. No. Des. 295,445. This tool includes a generally cylindrical body with a relatively pointed dilator tip at one end and a fine cylindrical member at the opposite end which carries an encircling, telescoping sleeve.

Figure 20C:
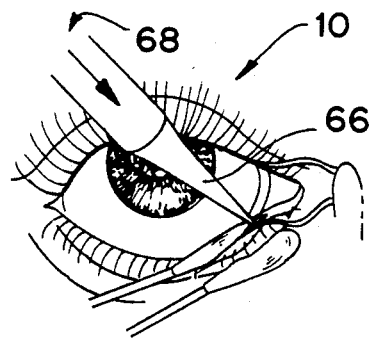

As shown in FIG. 20C, the punctum is carefully dilated with the pointed dilator end 66 of the dilator/inserter 68. To facilitate penetration of the punctum, the tip of the dilator end 66 may be moistened in a saline solution and slowly rotated and projected coaxially into the canaliculus.

Figure 20D:
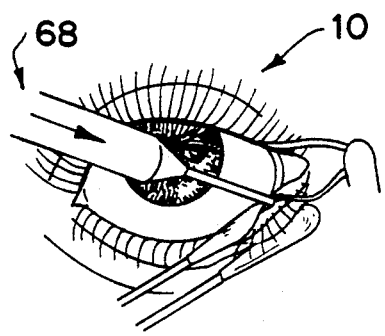
Figure 20E:
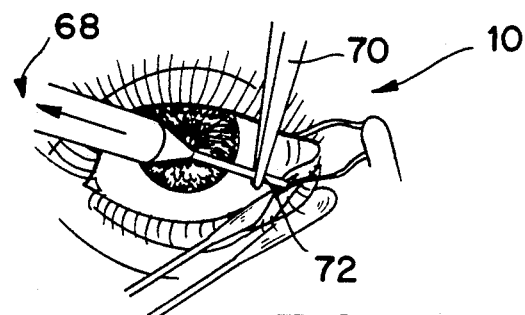

Referring now to FIG. 20D, the punctum plug 22 is positioned upon the cylindrical tip of the inserter 68 by friction engagement. More specifically, the tip is inserted into the insertion port 32 and is held there by friction engagement. The inserter is then used to position the plug 22 through the punctum 18 and into the associated canaliculus until the arcuate head member 28 rests on top of the area surrounding the punctal aperture 18.

When the punctum plug 22 is positioned in the canaliculus, as indicated by FIG. 2, the inserter is withdrawn from the insertion port 32. Forceps 200 are used to grasp the outer sleeve 72 so that the tool 68 may be withdrawn as shown in FIG. 7E. The punctum plug 22 remains in position, as noted in FIG. 2.

At the time of insertion, the punctum plug is in a dehydrated, condensed state. The hydrophobic coating is flexible, and thus easily manipulated, and conforms in shape to the underlying dehydrated hydrogel to facilitate the insertion process. The punctum plug is operably inserted in a patient's canaliculus in a posture so that the placement and retaining member extends away from the punctal opening and the arcuate head remains adjacent to the exterior surface of the punctal opening. Once installed, the hydrogel material swells from the intake of canalicular fluid so that it contacts the sidewalls of the canaliculus.

The rigidity of the dehydrated plugs described in association with FIGS. 7, 8, 11, 12, 15, 16, and 19 permits a physician to use medical-grade forceps to grasp the head member of the plug and insert the plug into a patient's punctal aperture via the above-described procedure.

BRIEF SUMMARY OF MAJOR ADVANTAGES OF THE INVENTION

After reading and understanding the foregoing description of preferred embodiment of the subject punctum plug and method, in conjunction with the drawings, it will be appreciated that several distinct advantages of the subject invention are obtained.

Without attempting to set forth all of the desirable features of the instant punctum plug, at least some of the major advantages of the invention include the combination of a hydrogel material and a hydrophobic coating. More specifically, the use of a hydrophobic coating, such as medical grade silicone, prevents the hydrogel from coming in contact with denatured proteinaceous substances and thereby obviates the possibility of an adverse tissue response. The flexibility of the coating permits the coating to conform to the shape of the underlying hydrogel material in either hydrated or dehydrated state. Additionally, use of a hydrogel material, such as polyHEMA, permits the plug to be inserted in a dehydrated, condensed state and therefore reduces the degree of necessary punctal dilation.

The configuration of the punctum plug includes a generally cylindrical body portion 26, an arcuate head member 28, and a placement and retaining member 30. The arcuate head member 28 insures that the punctum plug 22 will remain in position and will not slip into an associated canaliculus. The insertion port 32 fashioned in the arcuate head member 28 permits an inserter tool to engage with the punctum plug 22 and be facilely inserted through a punctal aperture.

The placement and retaining member 30 maintains the position of the punctum plug 22 by preventing the plug from being dislodged from the canaliculus. Moreover, the conical outer surface 34, which is tapered at the end of the placement and retaining member 30, facilitates insertion of the punctum plug 22 by gradually expanding the canaliculus. Similarly, a second embodiment of a punctum plug 42 discloses a multi-stepped placement and retaining member 50 having first 52 and second 54 stepped portions. The second stepped portion 54 is tapered similar to the punctum plug 22 and permits the plug to be facilely inserted.

The hydrating port and bore 38 permits canalicular and preocular tear film (PTF) fluid to hydrate the hydrogel material. The plug is expanded and occludes the punctal opening. The cavity walls 40 of the hydrating port 38 are not coated with the hydrophobic coating so that fluid may permeate the hydrogel material of the punctum plug.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which will fall within the purview of the subject invention and claims.

What is claimed is:

1. A punctum plug for blocking lacrimal fluid flow through a punctal aperture and into an associated canaliculus of a human eye comprising:

a generally cylindrical body member composed of a hydrogel material and having, a first end operable to be positioned adjacent the punctal aperture, and a second end operable to be positioned through the punctal aperture and into an associated canaliculus;

a head member composed of a hydrogel material and integrally joined to said generally cylindrical body member positioned at said first end of said generally cylindrical body member, the diameter of said head member at the junction with said generally cylindrical body member being greater than the diameter of said generally cylindrical body member so that an annular ridge is formed between said head member and said generally cylindrical body member, said annular ridge being operable to rest on a surface surrounding the punctal aperture to prevent said punctum plug from migrating into the associated canaliculus;

a placement and retaining member composed of a hydrogel material and integrally joined to said generally cylindrical body member and positioned at said second end of said generally cylindrical body member for facilitating placement of said generally cylindrical body member through the punctal aperture of a patient and for retaining said generally cylindrical body member within the associated canaliculus;

a hydrophobic coating covering the exterior surface of said head member, said generally cylindrical body member, and said placement and retaining member, said hydrophobic coating isolating said hydrogel material from physical contact with the canalicular tissue of a patient; and hydrating means fashioned through said hydrophobic coating for permitting placement of said punctum plug into position in a dehydrated, relatively rigid condition and then permitting, in situ, hydration of said hydrogel material of said punctum plug, said hydrating means serving to admit lacrimal fluid into said hydrogel material of said punctum plug to hydrate said punctum plug into an expanded, relatively flexible condition.

2. A punctum plug as defined in claim 1 wherein said hydrating means comprises:
a hydrating bore extending through said hydrophobic coating and into said placement and retaining member and being coaxial with respect to said generally cylindrical body member, said hydrating bore operably facilitating the intake of lacrimal fluid into said hydrogel material of said punctum plug so that said punctum plug expands, in situ, and is securely positioned within the associated canaliculus of the patient to block the passage of lacrimal fluid away from a patient's eye.

3. A punctum plug as defined in claim 2 wherein:
said placement and retaining member is generally conical in configuration and has a base positioned at said second end of said generally cylindrical body member and a conical exterior surface extending away from said second end; and
the diameter of said base is greater than the diameter of said generally cylindrical body member such that a second annular ridge is formed adjacent to said second end of said generally cylindrical body member for operably retaining said punctum plug within a patient's canaliculus.

4. A punctum plug as defined in claim 2 wherein said placement and retaining member comprises:
a cone-shaped portion extending away from said second end of said generally cylindrical body member; and
a stepped portion formed in the shape of a truncated cone and positioned between said second end and said cone-shaped portion.

5. A punctum plug as defined in claim 2 and further comprising:
an insertion bore for receiving an insertion tool, said insertion bore partially extending into said head member in a direction coaxial with said generally cylindrical body member, the interior surfaces of said insertion bore being coated with said hydrophobic material.

6. A punctum plug as defined in claim 2 and further comprising:
an insertion bore for receiving an insertion tool, said insertion bore extending axially into said head member and coaxially with respect to said generally cylindrical body member, said insertion bore extending through said hydrophobic coating an operably admitting lacrimal fluid into said head member to swell the dimensions of said punctum plug.

7. A punctum plug as defined in claim 5 wherein:
said head member is hemispherical in shape and has a base integrally joined to said first end of said generally cylindrical body member and an arcuate surface extending away from said first end.

8. A punctum plug as defined in claim 1 wherein:
said placement and retaining member is formed in the configuration of a truncated cone and has a base positioned at said second end of said generally cylindrical body member, a conical exterior surface extending away from said second end, and a distal end opposite said base.

9. A punctum plug as defined in claim 8 wherein said hydrating means comprises:
a port extending through said hydrophobic coating to admit canalicular fluid into said hydrogel material of said punctum plug.

10. A punctum plug as defined in claim 8 wherein said hydrating means comprises:
a hydrating bore extending through said hydrophobic coating and into said placement and retaining member through said distal end and coaxial with respect to said generally cylindrical body member.

11. A punctum plug as defined in claim 9 and further comprising:
an insertion bore for receiving an insertion tool, said insertion bore extending axially into said head member and said generally cylindrical body member and further extending partially into said placement and retaining member, said insertion port extending coaxially with said generally cylindrical body member.

12. A punctum plug as defined in claim 11 wherein:
said insertion bore is provided with a hydrophobic coating.

13. A punctum plug as defined in claim 10 and further comprising:
an insertion bore for receiving an insertion tool, said insertion bore extending axially through said head member and partially through said generally cylindrical body member, said insertion bore being coaxial with said hydrating bore.

14. A punctum plug as defined in any one of claims 1, 9, 10, 11, and 13 wherein:
said head member has a generally planar central exterior surface and has a height dimension less than $\frac{1}{8}$ the diameter of said generally cylindrical body member.

15. A punctum plug as defined in claim 1 wherein:
said hydrogel material is composed of hydroxyethylmethacrylate.

16. A punctum plug as defined in claims 1 and 15 wherein:
said hydrophobic coating is composed of medical grade silicone.

17. A punctum plug as defined in claim 1 wherein:
said hydrophobic coating is impermeable to lacrimal fluid.

18. A punctum plug for blocking lacrimal fluid flow through a punctal aperture and into an associated canaliculus of a human eye comprising:
a generally cylindrical body member composed of a hydrogel material and having an arcuate and concave lateral side surface dimensioned to generally conform to and receive a punctum of a patient's eye;
an arcuate head member composed of a hydrogel material integrally joined to a first end of said body member for positioning adjacent an exterior surface of the punctal aperture;
a placement member composed of a hydrogel material integrally joined to a second end of said body member for facilitating placement of said body member through the punctal aperture and into the associated canaliculus of the patient;
a hydrophobic coating covering the exterior surface of said head member, said generally cylindrical body member, and said placement, said hydrophobic coating isolating said hydrogel material from initiating contact with the canalicular tissue of a patient; and hydrating means fashioned through said hydrophobic coating for permitting placement of said punctum plug into position in a dehydrated, relatively rigid condition and then permitting, in situ, hydration of said hydrogel material of said punctum plug, said hydrating means serving to admit lacrimal fluid into said hydrogel material of said punctum plug to hydrate said punctum plug into an expanded and relatively rigid condition.

19. A punctum plug as defined in claim 18 wherein:
said placement member is formed in a truncated cone shape; and
said placement member has a conical exterior surface extending away from said body member terminating in a distal end.

20. A punctum plug as defined in claim 19 wherein said hydrating means comprises:
a port fashioned through said hydrophobic coating at said distal end of said placement member to admit lacrimal fluid into said hydrogel material of said punctum plug.

21. A punctum plug as defined in claim 20 and further comprising:
an insertion bore for receiving an insertion tool, said insertion bore extending axially through said arcuate head member and said body member having an arcuate and concave lateral side surface and further extending partially into said placement member, said insertion port being coaxial with body member.

22. A punctum plug as defined in claim 21 wherein:
said hydrophobic coating extends into and covers the interior surfaces of said insertion bore.

23. A punctum plug as defined in claim 19 wherein said hydrating means comprises:
a hydrating bore extending through said hydrophylic coating into said placement member and being coaxial with respect to said body member, said hydrating port operably facilitating the intake of lacrimal fluid into said hydrogel material of said punctum plug.

24. A punctum plug as defined in claim 23 and further comprising:
an insertion bore for receiving an insertion tool, said insertion bore extending axially through said head member and partially through said body member, said insertion bore being coaxial with said hydrating bore.

25. A punctum plug as defined in claim 18 wherein:
said placement member is conical in shape and extends away from said body member and terminates in a tip,
said tip extending through a port formed through said hydrophobic coating to admit lacrimal fluid into said hydrogel material of said punctum plug.

* * * * *